(12) United States Patent
Kramer et al.

(10) Patent No.: US 6,628,988 B2
(45) Date of Patent: Sep. 30, 2003

(54) APPARATUS AND METHOD FOR REVERSAL OF MYOCARDIAL REMODELING WITH ELECTRICAL STIMULATION

(75) Inventors: Andrew P. Kramer, Stillwater, MN (US); Rodney W. Salo, Fridley, MN (US); Julio C. Spinelli, Shoreview, MN (US); Bruce H. KenKnight, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 190 days.

(21) Appl. No.: 09/844,256

(22) Filed: Apr. 27, 2001

(65) Prior Publication Data

US 2002/0161410 A1 Oct. 31, 2002

(51) Int. Cl.$^7$ .............................................. A61N 1/362
(52) U.S. Cl. ......................................................... 607/9
(58) Field of Search ............................................. 607/9

(56) References Cited

U.S. PATENT DOCUMENTS

| | | | |
|---|---|---|---|
| 4,354,497 A | 10/1982 | Kahn ..................... 128/419 D |
| 4,549,548 A | 10/1985 | Wittkampf et al. ... 128/419 PG |
| 4,554,922 A | 11/1985 | Prystowsky et al. ........ 128/419 |
| 4,628,934 A | 12/1986 | Pohndorf et al. ..... 128/419 PG |
| 4,674,518 A | 6/1987 | Salo ......................... 128/695 |
| 4,928,688 A | 5/1990 | Mower ................. 128/419 PG |
| 5,058,605 A | 10/1991 | Slovak ....................... 128/783 |
| 5,156,149 A | 10/1992 | Hudrlik ................ 128/419 PG |
| 5,174,289 A | 12/1992 | Cohen .................. 128/419 PG |
| 5,233,985 A | 8/1993 | Hudrlik ........................ 607/27 |
| 5,267,560 A | 12/1993 | Cohen ......................... 607/25 |
| 5,370,665 A | 12/1994 | Hudrlik .......................... 607/9 |
| 5,514,161 A | 5/1996 | Limousin ....................... 607/9 |
| 5,584,867 A | 12/1996 | Limousin et al. ............... 607/9 |
| 5,674,259 A | 10/1997 | Gray ............................ 607/20 |
| 5,792,203 A | 8/1998 | Schroeppel .................... 607/30 |
| 5,797,970 A | 8/1998 | Pouvreau ........................ 607/9 |
| 5,935,160 A | 8/1999 | Auricchio et al. ........... 607/122 |
| 5,995,870 A | 11/1999 | Cazeau et al. .................. 607/9 |
| 5,995,871 A | 11/1999 | Knisley ........................ 607/15 |
| 6,223,082 B1 | 4/2001 | Bakels et al. .................. 607/17 |
| 6,314,322 B1 * | 11/2001 | Rosenberg .................... 607/17 |
| 6,363,279 B1 | 3/2002 | Ben-Haim et al. .............. 607/9 |
| 6,556,872 B2 * | 4/2003 | Hauck .......................... 607/62 |
| 2002/0082647 A1 | 6/2002 | Alferness et al. | |

FOREIGN PATENT DOCUMENTS

| | | | |
|---|---|---|---|
| EP | 0522693 | 1/1993 | ............ A61N/1/39 |
| WO | 00/09206 | 2/2000 | .......... A61N/1/362 |

OTHER PUBLICATIONS

Braunwald, et al., "Sustained Paired Electrical Stimuli; Slowing of the Ventricular Rate and Augmentation of Contractile Force", *American Journal of Cardiology* 14, pp. 285 & 385–393, (1964).

Sabbath, et al., "Delivery of Non–Excitatory Contractility–Modulation Electric Signals Improve Left Ventricular Performance in Dogs with Heart Failure", *Circulation, Supplement* 1, 100 (18), Abstract No. 631, pp. I–122, (Nov. 2, 1999).

* cited by examiner

*Primary Examiner*—Carl Layno
(74) *Attorney, Agent, or Firm*—Schwegman, Lundberg, Woessner & Kluth, P.A.

(57) ABSTRACT

An apparatus and method for reversing ventricular remodeling with electro-stimulatory therapy. A ventricle is paced by delivering one or more stimulatory pulses in a manner such that a stressed region of the myocardium is pre-excited relative to other regions in order to subject the stressed region to a lessened preload and afterload during systole. The unloading of the stressed myocardium over time effects reversal of undesirable ventricular remodeling.

20 Claims, 2 Drawing Sheets

APPARATUS AND METHOD FOR REVERSAL OF MYOCARDIAL REMODELING WITH ELECTRICAL STIMULATION

FIELD OF THE INVENTION

This invention pertains to apparatus and methods for electrostimulation of the heart including cardiac pacing with an artificial pacemaker. In particular, the invention relates to a method and apparatus for stimulating the heart in order to effect reversal of myocardial remodeling.

BACKGROUND

Congestive heart failure (CHF) is a clinical syndrome in which an abnormality of cardiac function causes cardiac output to fall below a level adequate to meet the metabolic demand of peripheral tissues. CHF can be due to a variety of etiologies with that due to ischemic heart disease being the most common. Inadequate pumping of blood into the arterial system by the heart is sometimes referred to as "forward failure," with "backward failure" referring to the resulting elevated pressures in the lungs and systemic veins which lead to congestion. Backward failure is the natural consequence of forward failure as blood in the pulmonary and venous systems fails to be pumped out. Forward failure can be caused by impaired contractility of the ventricles or by an increased afterload (i.e., the forces resisting ejection of blood) due to, for example, systemic hypertension or valvular dysfunction. One physiological compensatory mechanism that acts to increase cardiac output is due to backward failure which increases the diastolic filling pressure of the ventricles and thereby increases the preload (i.e., the degree to which the ventricles are stretched by the volume of blood in the ventricles at the end of diastole). An increase in preload causes an increase in stroke volume during systole, a phenomena known as the Frank-Starling principle. Thus, heart failure can be at least partially compensated by this mechanism but at the expense of possible pulmonary and/or systemic congestion.

When the ventricles are stretched due to the increased preload over a period of time, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium which leads to alterations in cellular structure, a process referred to as ventricular remodeling. Hypertrophy can increase systolic pressures but also decreases the compliance of the ventricles and hence increases diastolic filling pressure to result in even more congestion. It also has been shown that the sustained stresses causing hypertrophy may induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the process ultimately results in both systolic and diastolic dysfunction. It has been shown that the extent of ventricular remodeling is positively correlated with increased mortality in CHF patients. It is with reversing such ventricular remodeling that the present invention is primarily concerned.

SUMMARY OF THE INVENTION

The present invention relates to an apparatus and method for reversing ventricular remodeling with electrostimulatory therapy. In accordance with the invention, a ventricle is paced by delivering one or more stimulatory pulses in a manner such that a previously stressed and remodeled region of the myocardium is pre-excited relative to other regions in order to subject the region to a lessened preload and afterload during systole. By unloading the region in this way over a period of time, reversal of undesirable ventricular remodeling is effected. Pre-excitation may also be applied to stressed regions of the myocardium that have been weakened by ischemia or other causes in order to prevent further dilation and/or promote healing.

The ventricular stimulatory pulse or pulses may be delivered in accordance with a programmed bradycardia pacing mode in response to sensed cardiac activity and lapsed time intervals. In one embodiment, a stimulating/sensing electrode is disposed in the ventricle at a selected site in proximity to a stressed region. Pacing that pre-excites the ventricle at this site results in the stressed region being excited before other regions of the ventricular myocardium as the wave of excitation spreads from the paced site. Other embodiments involve multi-site pacing in which a plurality of stimulating/sensing electrodes are disposed in the ventricles. Pacing the ventricles during a cardiac cycle then involves outputting pulses to the electrodes in a specified sequence. In accordance with the invention, the pulse output sequence may be specified such that a stressed region of the ventricular myocardium is excited before other regions as the wave of excitation spreads from the multiple pacing sites.

For example, in multi-site univentricular pacing, a plurality of stimulating/sensing electrodes are provided for a single ventricle. Stimulatory pulses are then delivered through each electrode in a specified pulse output sequence in order to pace the ventricle during a cardiac cycle. In a pacemaker configured for biventricular pacing therapy, stimulating/sensing electrodes are provided for both the left and right ventricles such that the ventricles are then paced during a cardiac cycle by the delivery of both right and left ventricular stimulatory pulses if not inhibited by intrinsic activity. The timing of the right and left ventricular stimulatory pulses may be specified by a pulse output sequence that includes an interventricular delay interval defining in what order the ventricles are paced and the time delay between the paces. With either multi-site univentricular pacing or biventricular pacing, the pulse output sequence can be specified so as to excite a stressed region of the myocardium earlier than other regions by a pre-excitation time interval.

The pulse output sequence of a multi-site pacemaker may be initially specified by a clinician in accordance with regional measurements of myocardial mass so that stressed regions are excited first during a paced cardiac cycle. In another embodiment, an implanted device may automatically adjust the pulse output sequence in accordance with measurements of conduction delays or impedance measurements that reflect regional variations in myocardial mass or intrinsic conduction sequence.

The pulse output sequence best suited for reversal of remodeling may not be the optimum pulse output sequence for maximizing hemodynamic performance. In another embodiment, therefore, the pulse output sequence is adjusted automatically in accordance with activity level measurements reflective of metabolic demand. The pulse output sequence is then alternated between one designed to produce hemodynamically more effective contractions when metabolic needs of the body are great to one designed for remodeling reversal when metabolic needs are less.

DETAILED DESCRIPTION

Figure 1:
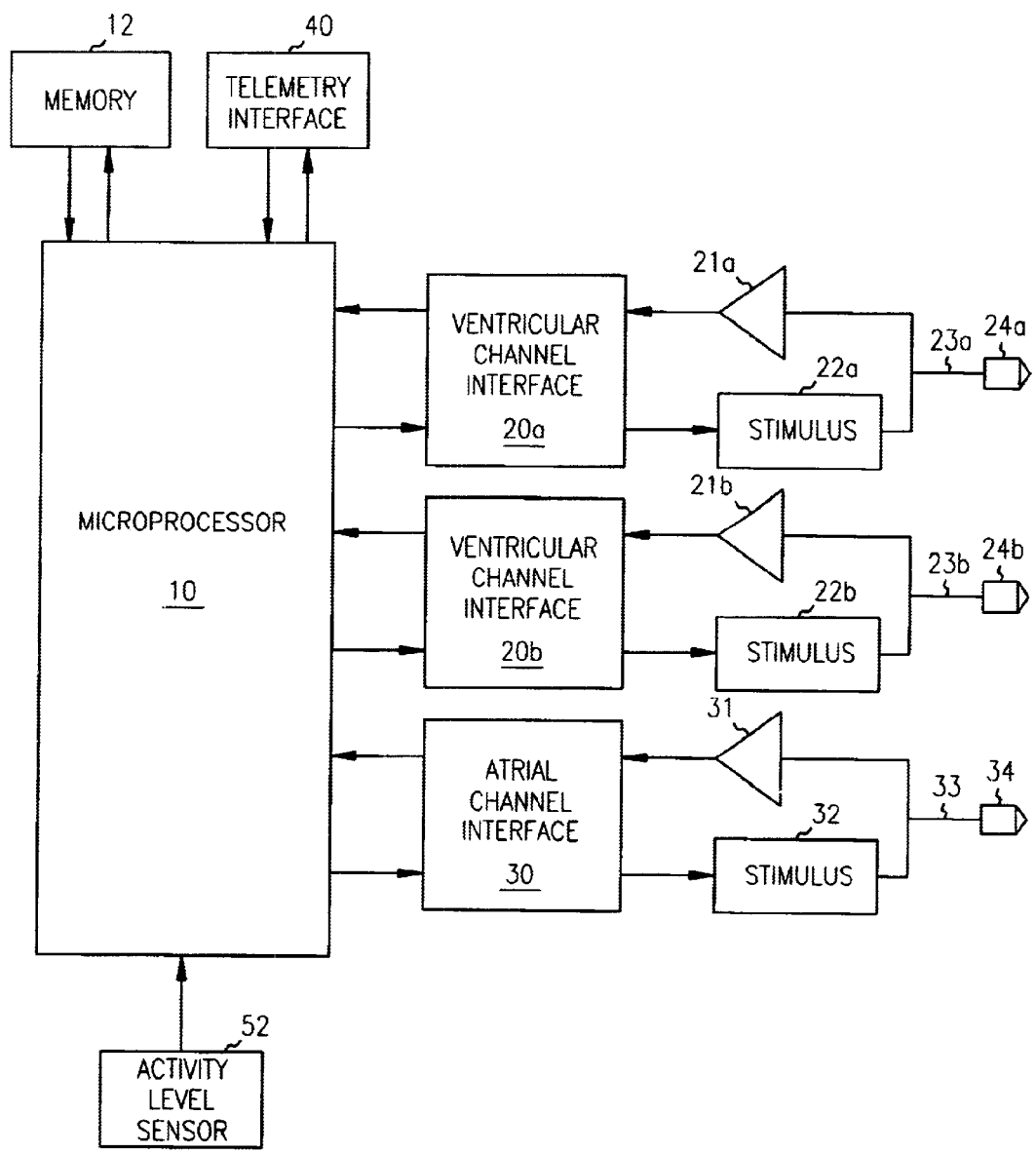
FIG. 1 is a block diagram of an exemplary cardiac rhythm management device for practicing the present invention.

Conventional cardiac pacing with implanted pacemakers involves excitatory electrical stimulation of the heart by an electrode in electrical contact with the myocardium. (As the term is used herein, "excitatory stimulation" refers to stimulation sufficient to cause contraction of muscle fibers, which is also commonly referred to as pacing. Furthermore, the term "pacemaker" should be taken to mean any cardiac rhythm management device with a pacing functionality, regardless of any other functions it may perform such as cardioversion/defibrillation or drug delivery.) The pacemaker is usually implanted subcutaneously on the patient's chest, and is connected to an electrode for each paced heart chamber by leads threaded through the vessels of the upper venous system into the heart. In response to sensed electrical cardiac events and elapsed time intervals, the pacemaker delivers to the myocardium a depolarizing voltage pulse of sufficient magnitude and duration to cause an action potential. A wave of depolarizing excitation then propagates through the myocardium, resulting in a heartbeat.

Some form of cardiac pacing can often benefit CHF patients. For example, sinus node dysfunction resulting in bradycardia can contribute to heart failure which can be corrected with conventional bradycardia pacing. Also, some CHF patients suffer from some degree of AV block such that their cardiac output is improved by synchronizing atrial and ventricular contractions with dual-chamber pacing using a programmed AV delay time (i.e., atrial triggered ventricular pacing or AV sequential pacing). CHF patients may also suffer from conduction defects of the specialized conduction system of the heart (a.k.a. bundle branch blocks) so that a depolarization impulse from the AV node reaches one ventricle before the other. Stretching of the ventricular wall brought about by CHF can also cause slowed conduction of depolarization impulses through the ventricle. If conduction velocity is slowed in the left ventricle more than the right, for example, the contraction of the two ventricles during ventricular systole becomes uncoordinated which lessens pumping efficiency. In both of these situations, cardiac output can be increased by improving the synchronization of right and left ventricular contractions. Cardiac pacemakers have therefore been developed which provide pacing to both ventricles. (See, e.g., U.S. Pat. No. 4,928,688, issued to Mower and hereby incorporated by reference.)

The specialized His-Purkinje conduction network of the heart rapidly conducts excitatory impulses from the sino-atrial node to the atrio-ventricular node, and thence to the ventricular myocardium to result in a coordinated contraction of both ventricles. Artificial pacing with an electrode fixed into an area of the myocardium does not take advantage of the heart's normal specialized conduction system for conducting excitation throughout the ventricles. This is because the specialized conduction system can only be entered by impulses emanating from the atrio-ventricular node. Thus the spread of excitation from a ventricular pacing site must proceed only via the much slower conducting ventricular muscle fibers, resulting in the part of the ventricular myocardium stimulated by the pacing electrode contracting well before parts of the ventricle located more distally to the electrode. Although the pumping efficiency of the heart is somewhat reduced from the optimum, most patients can still maintain more than adequate cardiac output with artificial pacing.

In multi-site pacing, the atria or ventricles are paced at more than one site in order to effect a spread of excitation that results in a more coordinated contraction. Biventricular pacing, as described above, is one example of multi-site pacing in which both ventricles are paced in order to synchronize their respective contractions. Multi-site pacing may also be applied to only one chamber. For example, a ventricle may be paced at multiple sites with excitatory stimulation pulses in order to produce multiple waves of depolarization that emanate from the pacing sites. This may produce a more coordinated contraction of the ventricle and thereby compensate for intraventricular conduction defects that may exist. Stimulating one or both ventricles with multi-site pacing in order to improve the coordination of the contractions and overcome interventricular or intraventricular conduction defects is termed resynchronization therapy.

Altering the coordination of ventricular contractions with multi-site pacing can also be used to deliberately change the distribution of wall stress experienced by the ventricle during the cardiac pumping cycle. The degree to which a heart muscle fiber is stretched before it contracts is termed the preload. The maximum tension and velocity of shortening of a muscle fiber increases with increasing preload. The increase in contractile response of the heart with increasing preload is known as the Frank-Starling principle. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region that contracts later than other regions is subjected to both an increased preload and afterload. This situation is created frequently by the ventricular conduction delays associated with heart failure and ventricular dysfunction.

The heart's initial physiological response to the uneven stress resulting from an increased preload and afterload is compensatory hypertrophy in those later contracting regions of the myocardium. In the later stages of remodeling, the regions may undergo atrophic changes with wall thinning due to the increased stress. The parts of the myocardium that contract earlier in the cycle, on the other hand, are subjected to less stress and are less likely to undergo hypertrophic remodeling. The present invention makes use of this phenomena in order to effect reversal of remodeling by pacing one or more sites in a ventricle (or an atrium) with one or more excitatory stimulation pulses during a cardiac cycle with a specified pulse output sequence. The pace or paces are delivered in a manner that excites a previously stressed and remodeled region of the myocardium earlier during systole so that it experiences less afterload and preload. This pre-excitation of the remodeled region relative to other regions unloads the region from mechanical stress and allows reversal of remodeling to occur.

In another application of the invention, pre-excitation stimulation may be used to unload a stressed myocardial region that has been weakened by ischemia or other causes. Such regions of the myocardium may be particularly vulnerable to dilation and formation of aneurysms. An increased preload and afterload also requires an increased energy expenditure by the muscle which, in turn, increases its perfusion requirements and may result in further ischemia. Pre-excitation of an ischemic region may thus reduce the region's need for blood as well as reduce the mechanical stress to which the region is subjected during systole to reduce the likelihood of further dilation.

A block diagram of a cardiac rhythm management device suitable for practicing the present invention is shown in FIG. 1. The controller of the device is made up of a microprocessor 10 communicating with a memory 12 via a bidirectional data bus, where the memory 12 typically comprises a ROM (read-only memory) for program storage and a RAM (random-access memory) for data storage. The controller could also include dedicated circuitry either instead of, or in addition to, the programmed microprocessor for controlling the operation of the device. The device has atrial sensing/stimulation channels comprising electrode 34, lead 33, sensing amplifier 31, pulse generator 32, and an atrial channel interface 30 which communicates bidirectionally with a port of microprocessor 10. The device also has multiple ventricular sensing/stimulation channels for delivering multi-site univentricular or biventricular pacing. Two such ventricular channels are shown in the figure that include electrodes 24a–b, leads 23a–b, sensing amplifiers 21a–b, pulse generators 22a–b, and ventricular channel interfaces 20a–b where "a" designates one ventricular channel and "b" designates the other. For each channel, the same lead and electrode may be used for both sensing and stimulation. The channel interfaces 20a–b and 30 may include analog-to-digital converters for digitizing sensing signal inputs from the sensing amplifiers and registers which can be written to by the microprocessor in order to output stimulation pulses, change the stimulation pulse amplitude, and adjust the gain and threshold values for the sensing amplifiers. A telemetry interface 40 is provided for communicating with an external programmer.

The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. Rate-adaptive pacing modes can also be employed where the ventricular and/or atrial escape intervals are modulated based upon measurements corresponding to the patient's exertion level. As shown in FIG. 1, an activity level sensor 52 (e.g., a minute ventilation sensor or accelerometer) provides a measure of exertion level to the controller for pacing the heart in a rate-adaptive mode. Multiple excitatory stimulation pulses can also be delivered to multiple sites during a cardiac cycle in order to both pace the heart in accordance with a bradycardia mode and provide resynchronization of contractions to compensate for conduction defects. In accordance with the invention, the controller may also be programmed to deliver stimulation pulses in a specified pulse output sequence in order to effect reduction of stress to a selected myocardial region.

Figure 2A:
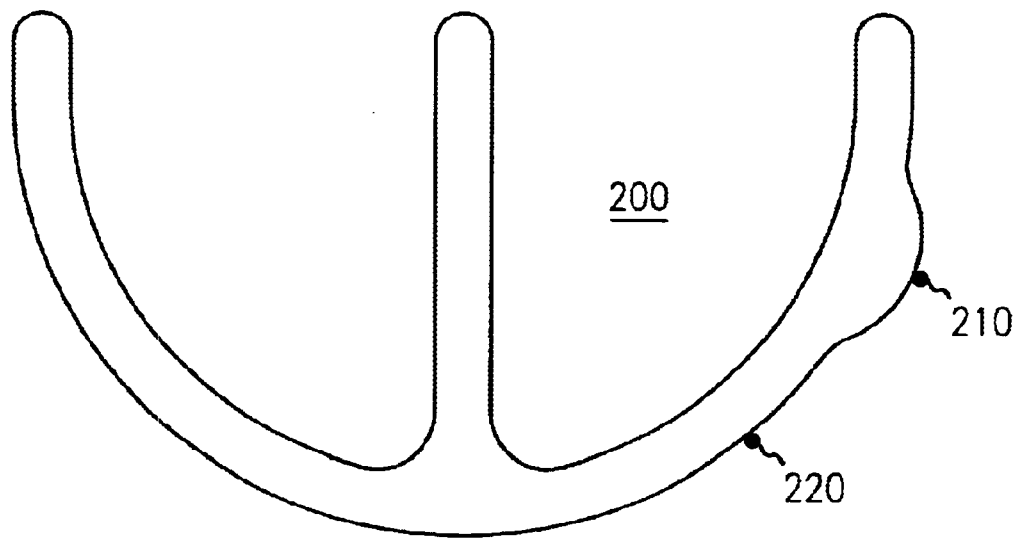
FIGS. 2A–B are diagrams showing exemplary placements of sensing/pacing electrodes.
Figure 2B:
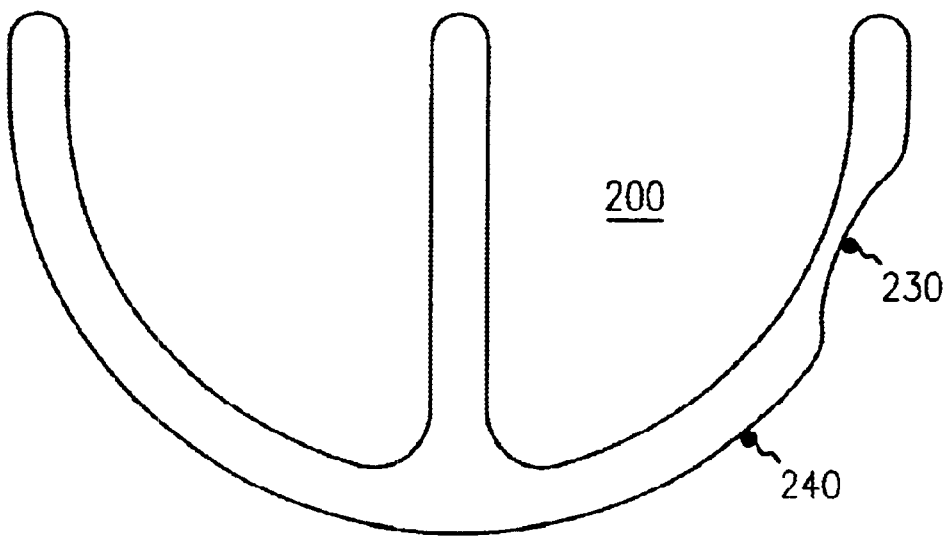

The invention may be beneficially applied to unload a stressed myocardial region that is either hypertrophied or thinned. FIG. 2A depicts a left ventricle 200 with pacing sites 210 and 220 to which may be fixed epicardial stimulation/sensing electrodes. The myocardium at pacing site 210 is shown as being hypertrophied as compared to the myocardium at pacing site 220. A cardiac rhythm management device such as shown in FIG. 1 may deliver stimulation pulses to both sites in accordance with a pacing mode through its ventricular stimulation/sensing channels. In order to unload the hypertrophied site 210 during systole and thereby promote reversal of the hypertrophy, the ventricle is paced with a pulse output sequence that stimulates the hypertrophied site 210 before the other site 220. The lessened mechanical stress during systole then allows the site 210 to undergo reversal of the hypertrophy. FIG. 2B shows a left ventricle 200 in which the pacing site 240 is relatively normal while the site 230 is a myocardial region that has been thinned due to late state remodeling or other stresses such as ischemia. Again, pacing of the ventricle with pre-excitation stimulation of site 230 relative to the site 240 unloads the thinned region and subjects it to less mechanical stress during systole. The result is either reversal of the remodeling or reduction of further wall thinning.

In one embodiment, a pre-excitation stimulation pulse is applied to a stressed region either alone or in a timed relation to the delivery of a stimulation pulse applied elsewhere to the myocardium. For example, both the right and left ventricles can be paced at separate sites by stimulation pulses delivered with a specified interventricular delay between the pulses delivered to each ventricle. By adjusting the interventricular delay so that one of the ventricular pacing sites is pre-excited relative to the other, the spread of activation between the two pacing sites can be modified to change the wall stresses developed near these sites during systolic contraction. Other embodiments may employ multiple electrodes and stimulation channels to deliver pulses to multiple pacing sites located in either of the atria or the ventricles in accordance with a specified pulse output sequence. A multi-site pacemaker may also switch the output of pacing pulses between selected electrodes or groups of electrodes during different cardiac cycles. Pacing is then delivered to a heart chamber through a switchable configuration of pacing electrodes, wherein a pulse output configuration is defined as a specific subset of a plurality of electrodes fixed to the paced chamber and to which pacing pulses are applied as well as the timing relations between the pulses. A plurality of different pulse output configurations may be defined as subsets of electrodes that can be selected for pacing. By switching the pulse output configuration to a different configuration, pacing to the heart chamber is thereby temporally distributed among the total number of fixed electrodes. The principle remains the same in these embodiments, however, of unloading a stressed myocardial site by pre-exciting it relative to other regions of the myocardium.

In other embodiments, a stressed region of the ventricular myocardium is pre-excited in a timed relation to a triggering event that indicates an intrinsic beat has either occurred or is imminent. For example, a pre-excitation stimulation pulse may be applied to a stressed region immediately following the earliest detection of intrinsic activation elsewhere in the ventricle. Such activation may be detected from an electrogram with a conventional ventricular sensing electrode. An earlier occurring trigger event may be detected by extracting the His bundle conduction potential from a special ventricular sensing electrode using signal processing techniques.

In order to deliver a pre-excitation stimulus to a stressed site at a time well before any intrinsic activation takes place at other sites, the stimulus can be applied after a specified AV delay interval following an atrial sense or atrial pace. The objective in this situation is to deliver the pre-excitation stimulus before the excitation from the atrio-ventricular node reaches the ventricles via the specialized conduction pathway. Accordingly, the normal intrinsic atrio-ventricular delay (e.g., the PR interval on an EKG or the equivalent electrogram interval recorded using implanted leads) can be measured, with the AV pacing delay interval then programmed to be shorter than the measured intrinsic AV delay interval by a specified pre-excitation interval. The AV pacing delay interval may be either fixed at some value (e.g., at 60 ms, with a variable range of 0–150 ms) or be made to vary dynamically with a measured variable such as heart rate or exertion level.

The AV pacing delay interval for delivering a pre-excitation stimulus following an atrial sense or pace may also be set in accordance with a measured intrinsic conduction delay interval between the site to be pre-excited and another ventricular site, referred to as a V—V interval. The objective in this case is to reverse the intrinsic conduction delay existing between the two sites by pacing with a similar delay of opposite sign. For example, the intrinsic conduction delay between a stressed ventricular site and an earlier excited site is measured. The stressed site is then pre-excited after an AV pacing delay interval following an atrial sense or pace that is set in accordance with the measured V—V interval. In one embodiment, the pre-excitation interval is set as a linear function of the V—V interval:

Pre-excitation interval=$(a)(V-V \text{ interval})+b$

The AV pacing delay interval is then computed by subtracting the pre-excitation interval from the measured intrinsic AV delay interval.

A clinician may use various techniques in order to determine areas that have undergone remodeling or are otherwise stressed. For example, ventricular wall thickness abnormalities and regional variations in myocardial mass may be observed with echocardiography or magnetic resonance imaging. Observation of akinetic or dyskinetic regions of the ventricle during contraction with an appropriate imaging modality may also be used to indicate stressed regions. Coronary angiograms indicating blood flow abnormalities and electrophysiological studies indicating regions of ischemia or infarction may be used to identify regions that have been stressed due to ischemia. Electrophysiological studies may also be used to determine regional conduction delays that can be reversed with pre-excitation stimulation. The pulse output sequence of a multi-site pacemaker or the interventricular delay of a biventricular pacemaker may then be initially specified in accordance with those findings so that stressed regions are excited first during a paced cardiac cycle.

In a further refinement, an implanted cardiac rhythm management device may automatically adjust the pulse output sequence in accordance with measurements of myocardial mass. Such measurements may be made by measuring the conduction delays of excitation spreading through the myocardium as sensed by multiple sensing/stimulation electrodes. Increased conductions delays through a region, for example, may be reflective of stress in the region that can be reduced by pre-excitation stimulation. In another embodiment, impedance measurements may be made between electrodes in proximity to the heart that correlate with variations in myocardial mass and contraction sequence. Such measurements may be used to identify akinetic or dyskinetic regions of the myocardium as well as to indicate wall thickness abnormalities. The particular pre-excitation interval used by the device may also be automatically adjusted in accordance with detected changes in the remodeling process. That is, the pre-excitation interval may be shortened as remodeling is reversed or increased as remodeling worsens. Remodeling changes can be detected by, for example, measuring changes or trends in conduction delays, contraction sequences, end-diastolic volume, stroke volume, ejection fraction, wall thickness, or pressure measurements.

In another embodiment, the pulse output sequence used by a cardiac rhythm management may be alternated between one designed to produce hemodynamically more effective contractions when metabolic needs of the body are great to one designed to promote reverse remodeling when metabolic needs are less. A pulse output sequence that unloads a hypertrophic region may not be the optimum pulse output sequence for maximizing hemodynamic performance. For example, a more hemodynamically effective contraction may be obtained by exciting all areas of the myocardium simultaneously, which may not effectively promote reversal of the hypertrophy or remodeling. The pulse output sequence may therefore be adjusted automatically in accordance with exertion level measurements reflective of metabolic demand so that pulse output sequences that unload hypertrophied or stressed regions are not used during periods of increased exertion.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A method for cardiac pacing, comprising:
   delivering a stimulatory pulse to a ventricular pacing site in response to sensed cardiac activity and lapsed time intervals in accordance with a programmed pacing mode, wherein a plurality of stimulating/sensing electrodes are disposed in the ventricles;
   wherein the pacing site is selected such that a stressed region of the ventricular myocardium is pre-excited relative to other regions in order to unload the stressed region and effect reversal of ventricular remodeling;
   pacing the ventricles during a cardiac cycle by outputting multiple pulses to the electrodes in a specified pulse output sequence; and,
   wherein the pulse output sequence is specified such that the stressed region of the ventricular myocardium is excited before other regions.

2. The method of claim 1 wherein the plurality of stimulating/sensing electrodes are disposed in a single ventricle.

3. The method of claim 1 wherein a stimulating/sensing electrode is disposed in both the left and right ventricles with right and left ventricular stimulatory pulses delivered in accordance with a specified interventricular delay interval, and further wherein the interventricular delay interval is specified so as to excite the stressed region of the myocardium first.

4. The method of claim 1 wherein the stimulatory pulse delivered to the stressed region is triggered by an atrial sense or pace.

5. The method of claim 1 further comprising adjusting the pulse output sequence in accordance with measurements of conduction delays that reflect regional variations in myocardial mass.

6. The method of claim 1 further comprising adjusting the pulse output sequence in accordance with thoracic impedance measurements that reflect regional variations in myocardial mass.

7. The method of claim 1 further comprising adjusting the pulse output sequence in accordance with thoracic impedance measurements that reflect variations in contraction sequence.

8. The method of claim 1 further comprising adjusting the pulse output sequence in accordance with activity level measurements reflective of metabolic demand so that the pulse output sequence is alternated between one designed to produce hemodynamically more effective contractions when metabolic needs of the body are great to one designed for remodeling reversal when metabolic needs are less.

9. The method of claim 1 wherein the stimulatory pulse delivered to the stressed region is triggered by a ventricular sense or pace.

10. A cardiac rhythm management device, comprising:
one or more ventricular sensing channels for sensing ventricular depolarizations and generating ventricular sense signals in accordance therewith;
a plurality of stimulatory channels for delivering stimulation to one or more ventricular pacing sites, the stimulatory channels including a plurality of stimulating/sensing electrodes for disposition in a single ventricle;
a controller for controlling the delivery of stimulatory pulses in accordance with a programmed pacing mode; and,
wherein the controller is programmed to pace one or more pacing sites during a cardiac cycle by delivering pulses in a specified pulse output sequence such that a stressed region of the ventricular myocardium is excited before other regions.

11. The device of claim 10 wherein the stimulatory channels include a stimulating/sensing electrode disposed in both the left and right ventricles, and wherein the controller is programmed to deliver right and left ventricular stimulatory pulses in accordance with a specified interventricular delay interval, with the interventricular delay interval specified so as to excite a stressed region of the myocardium before other regions of the myocardium.

12. The device of claim 10 wherein the pulse output sequence is specified in accordance with regional measurements of myocardial mass so that stressed regions are excited first during a paced cardiac cycle.

13. The device of claim 10 wherein the controller is programmed to adjust the pulse output sequence in accordance with measurements of conduction delays that reflect regional variations in myocardial mass.

14. The device of claim 10 further comprising a thoracic impedance sensor and wherein the controller is programmed to adjust the pulse output sequence in accordance with impedance measurements that reflect regional variations in myocardial mass.

15. The device of claim 10 further comprising an exertion level sensor and wherein the controller is programmed to adjust the pulse output sequence in accordance with activity level measurements reflective of metabolic demand so that the pulse output sequence is alternated between one designed to produce hemodynamically more effective contractions when metabolic needs of the body are great to one designed for remodeling reversal when metabolic needs are less.

16. The device of claim 10 further comprising a thoracic impedance sensor and wherein the controller is programmed to adjust the pulse output sequence in accordance with impedance measurements that reflect variations in contraction sequence.

17. A method for cardiac pacing, comprising:
delivering pacing pulses to a plurality of ventricular pacing sites in response to sensed cardiac activity and lapsed time intervals in accordance with a programmed pacing mode, wherein the plurality of ventricular pacing sites are disposed in the same ventricle;
pacing the ventricles during a cardiac cycle by outputting multiple pulses to the electrodes in a specified pulse output sequence; and,
wherein the pulse output sequence is specified such that the stressed region of the ventricular myocardium is excited before other regions.

18. The method of claim 17 further comprising adjusting the pulse output sequence in accordance with measurements of conduction delays that reflect regional variations in myocardial mass.

19. The method of claim 17 further comprising adjusting the pulse output sequence in accordance with thoracic impedance measurements that reflect regional variations in myocardial mass.

20. The method of claim 17 further comprising adjusting the pulse output sequence in accordance with thoracic impedance measurements that reflect variations in contraction sequence.

* * * * *